United States Patent [19]

Ferrante et al.

[11] Patent Number: 5,364,401
[45] Date of Patent: Nov. 15, 1994

[54] EXTERNAL ALIGNMENT SYSTEM FOR PREPARING A FEMUR FOR AN IMPLANT

[75] Inventors: Joseph M. Ferrante, Cordova; Dennis J. Buchanan, Memphis, both of Tenn.

[73] Assignee: Wright Medical Technology, Inc., Arlington, Tenn.

[21] Appl. No.: 957,991

[22] Filed: Oct. 8, 1992

[51] Int. Cl.$^5$ .................................. A61B 17/00
[52] U.S. Cl. ........................ 606/84; 606/79; 606/87; 606/88; 606/102
[58] Field of Search ............ 606/88, 87, 86, 102, 606/60, 62, 72, 74, 79, 80, 82, 84, 54, 57, 85

[56] References Cited

U.S. PATENT DOCUMENTS

| | | | |
|---|---|---|---|
| 2,291,413 | 7/1942 | Siebrandt | 606/103 |
| 4,457,307 | 7/1984 | Stillwell | 606/88 |
| 4,474,177 | 10/1984 | Whiteside | . |
| 4,487,203 | 12/1984 | Androphy | . |
| 4,703,751 | 11/1987 | Pohl | 606/87 |
| 4,907,578 | 3/1990 | Petersen | 606/79 |
| 4,952,213 | 8/1990 | Bowman et al. | 606/79 |
| 5,049,149 | 9/1991 | Schmidt | 606/87 |

FOREIGN PATENT DOCUMENTS

| | | | |
|---|---|---|---|
| 104732 | 4/1984 | European Pat. Off. | 606/88 |
| 243109 | 10/1987 | European Pat. Off. | 606/87 |
| 380451 | 8/1990 | European Pat. Off. | 606/88 |

OTHER PUBLICATIONS

Laskin, R. S. (1984), Orthopaedics 7, No. 1, pp. 36–46.
Surgical procedure entitled "Knee Replacement Using the Insall/Burstein Total Congular Knee System", issued by the New York Society for the Relief of the Ruptured and Crippled Children, Zimmer Orthopaedics, Warsaw, Ind.

*Primary Examiner*—Stephen C. Pellegrino
*Assistant Examiner*—Guy V. Tucker

[57] ABSTRACT

An article for preparing a bone to receive a distal implant includes a base having longitudinal axis, a support surface thereon, and seating surfaces for seating the base along a long axis of the bone. A pair of connected brackets are mounted on the base. A first of the brackets is axially adjustable relative to the longitudinal axis of the base and a second bracket is radially adjustable relative to the base. One of the brackets is operatively connected to the support surface and the other of the brackets includes a single point connecting mechanism for connecting a plurality of bone preparing devices to the base at a single point reference axially and radially adjustable relative to the base.

15 Claims, 6 Drawing Sheets

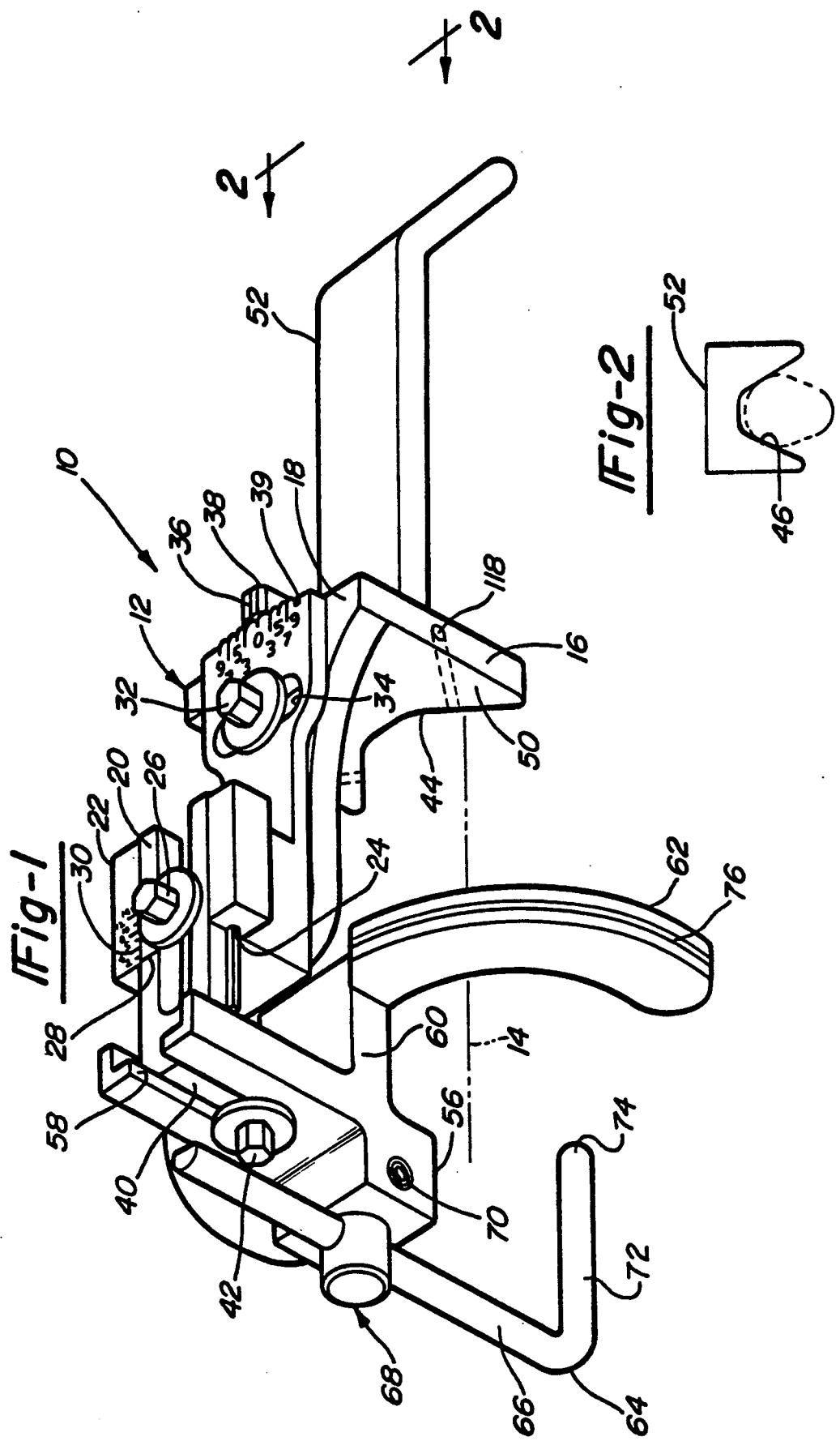

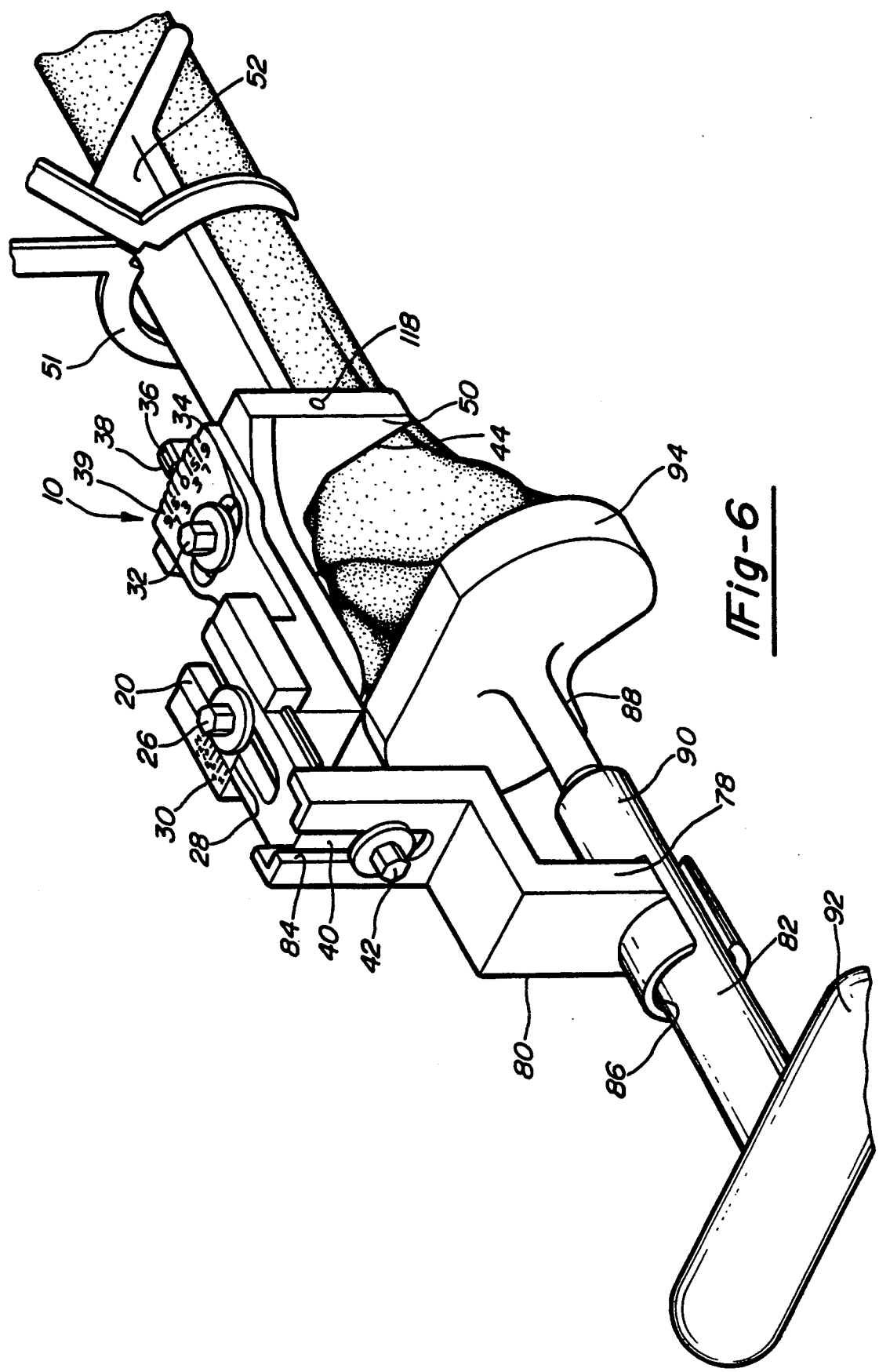

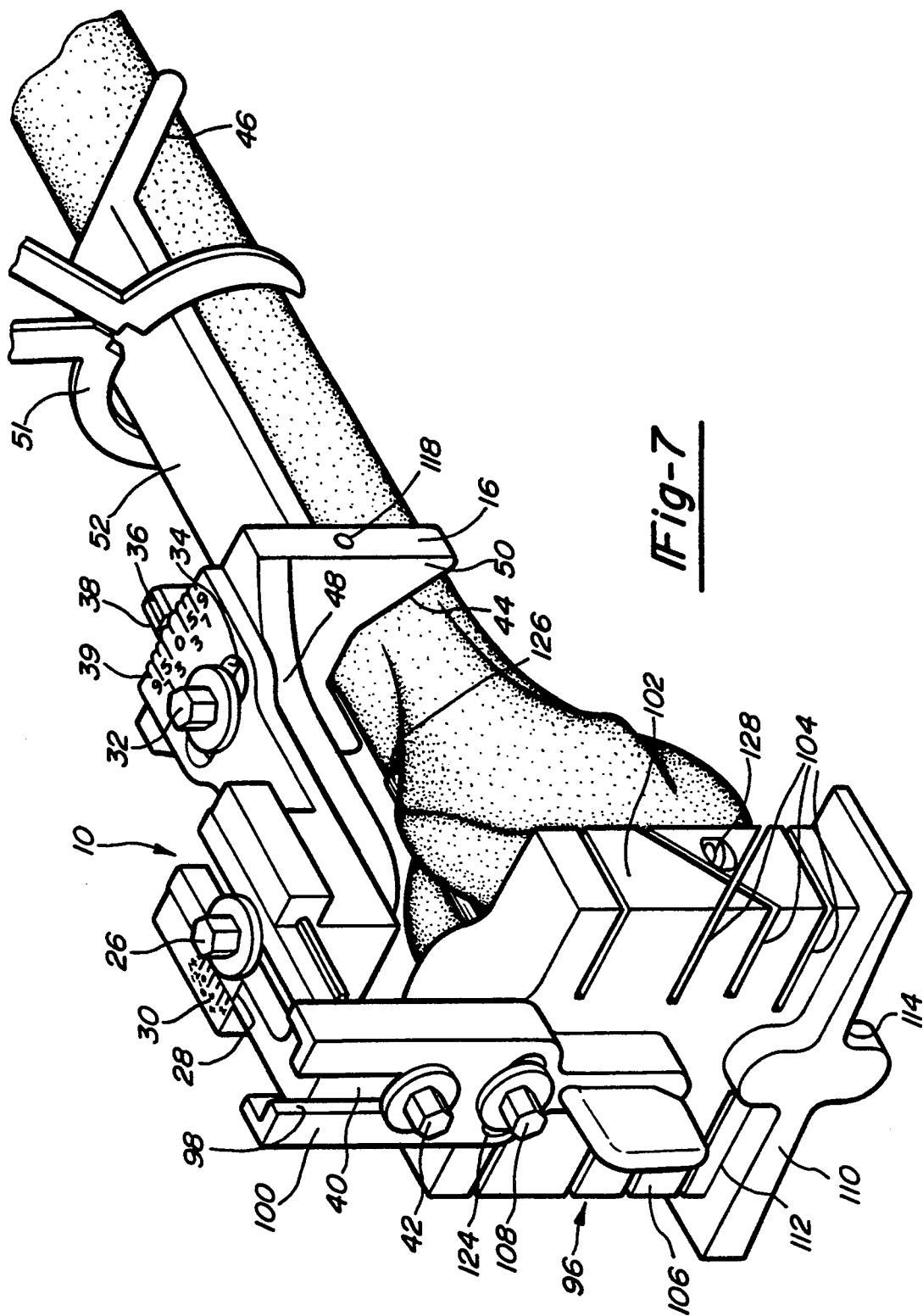

EXTERNAL ALIGNMENT SYSTEM FOR PREPARING A FEMUR FOR AN IMPLANT

TECHNICAL FIELD

The present invention generally relates to knee surgical resection techniques. More particularly, the present invention provides an article and method for preparing a bone, such as a femur, to receive a distal implant.

BACKGROUND OF THE INVENTION

Many surgical procedures have been developed involving the replacement of a knee joint with a prosthesis. Examples of such procedures are disclosed in the R.M.C. TM Total Knee System technical manual published by Richards Manufacturing Company, Inc. of Memphis, Tenn. and the Surgical Procedure for the Whiteside Ortholoc ® Modular Knee System Manual, published by the assignee of the present application. Each of the surgical protocols details the steps of exposing the knee joint and then preparing the distal femur and proximal tibia to enable the implantation of the prosthesis.

The alignment of the total knee components is an essential step in the performance of the total knee replacement arthroplasty. The article of R. S. Laskin, Orthopedics, January 1984, Vol. 7 No. 1, pp. 36–46, details various alignment systems, and an indepth discussion of the orientation of the knee joint and the criticality of the prosthesis reflecting an accurate varus or valgus angle for proper prosthesis placement.

Various instruments have been used to assist in alignment of the various distal cuts and anterior/posterior cuts made during the preparatory steps discussed above. For example, the U.S. Pat. No. 4,474,177 to Whiteside, issued Oct. 2, 1984 discloses a method and apparatus for shaping a distal femoral surface. The patent discusses a femoral surface modifying instrument in the form of a distal femoral condyle cutting guide. The U.S. Pat. No. 4,487,203 to Androphy, issued Dec. 11, 1984 discloses a single guide member for use in resecting the distal femoral condyles, the proximal tibia, and the distal femur. The surgical procedure entitled "Knee Replacement Using the Insall/Burstein Total Congular Knee System, issued by the New York Society for the Relief of the Ruptured and Crippled Children, Zimmer Orthopedics, Warsaw, Ind., discloses an operative procedure utilizing a spacer guide and a further cutter alignment instrument.

Each of the above patents and protocol provide alignment instruments which do not have the capability of axially and angularly aligning all preparatory instruments based on a single point which could thereby totally coordinate all preparatory cuts prior to final insertion of a trial or final femoral prosthesis component. Accordingly, various cuts, planings, and final placements are performed by estimations and purely eyeball estimations of appropriate angles and axial displacements of cuts.

The present invention provides a device and method allowing for accurately cutting the femur to accept femoral prothesis by providing a single point reference device that locates along the long axis of the femur and locks to it for referencing the external device to accurately place the cuts.

SUMMARY OF THE INVENTION

In accordance with the present invention, there is provided an article for preparing a bone to receive a distal implant, the device comprising a base having a longitudinal axis and mounting means for mounting the base on the bone aligning the longitudinal axis of the base parallel with a long axis of the bone. A single point connecting means connects a plurality of bone preparing devices to the base at a single point reference. Axial adjustment means axially adjust the single point connecting means relative to the longitudinal axis of the base and the long axis of the bone. Radial adjustment means radially adjusts the single point connecting means relative to the base and the distal end of the bone. Thusly, once the axial adjustment and radial adjustment are set, all bone preparing devices are connected the base reference to the same axial displacement and adjusted angle thereby providing complete consistency between each step to the surgical procedure.

The present invention further provides a method for preparing the distal end of a bone to receive the distal implant, the method generally including the steps of mounting a base member on the bone and clamping the base member along the long axis of the bone. One of a plurality of bone preparing devices are connected to the base member at a single reference point. The single reference point is axially and radially adjusted relative to the base member and long axis of the bone, thereby normalizing the axial and radial orientation of the bone preparing devices relative to the distal end of the bone.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is perspective view of the base member of the present invention having a distal cutting component mounted thereon;

FIG. 2 is an end on view of the apparatus shown in FIG. 1 taken substantially along lines 2—2 of FIG. 1;

FIG. 6 shows the base member having the planing component mounted thereon, the assembly being mounted on the distal end of the femur, the distal end of the femur having a distal cut made thereon; and FIG. 7 is a perspective view of the base member having the cutting block component mounted thereon, the assembly being mounted on the distal end of the femur, the distal end of the femur having been planed as shown in FIG. 6.

DETAILED DESCRIPTION OF THE INVENTION

Figure 3:
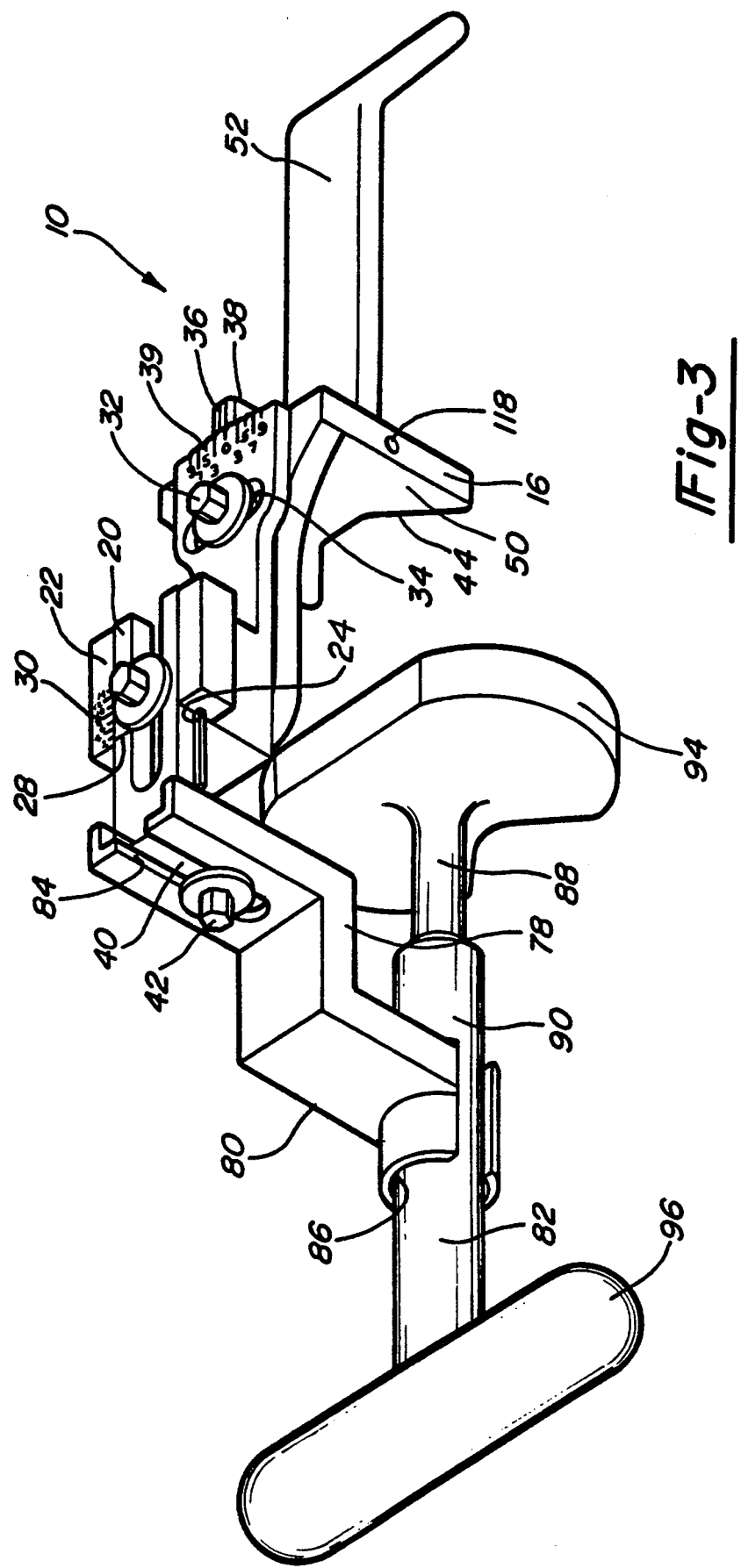
FIG. 3 is a perspective view of the base member having a planing cut component mounted thereon.

An article for preparing a bone to receive a distal implant is generally shown at 10 in the drawings. The article 10 as shown is specifically useful in preparing a femur to receive a distal femoral implant. However, the present invention can be modified in size for use in preparing various long bone distal surfaces to receive an implant.

The article 10 includes a base, generally shown at 12, having a longitudinal axis shown by hatch line 14. The base 12 includes a support member 16 which is L-shaped when viewed from its side and includes a top support surface 18. A pair of brackets 20,22 are mounted on the support surface 18. The first of the brackets 20 is axially adjustable relative to the longitudinal axis 14 of the base 12. The second of the brackets 22 is radially adjustable relative to the base 12. The second bracket 22 is operatively connected to the support surface 18 and the first of the brackets 20 is connected to the second bracket 22. These brackets could be connected in the reverse fashion wherein the first bracket 20 is designed to be connected to the mounting surface 18 and the second bracket 22 is designed to be connected to the first bracket 20.

The first bracket 20 is slidably supported within a groove track 24 in the second bracket 22. A lockscrew mechanism 26 fixes or sets the first bracket 20 in a desired position relative to the second bracket 22. An indicating line 28 on the top surface of the first bracket 20 cooperates with distance markings 30 on an adjoining top surface of the second bracket 22 to indicate the amount of relative axial movement between the first bracket 20 and the second bracket 22 for purposes described in detail below.

The second bracket 22 is pivotally mounted on the top surface 18 of the support member 16 by means well known in the art. Lockscrew mechanism 32 is disposed within an arcuate slot 34 of the second bracket 22 for setting and fixing a position of the second bracket 22 relative to the support member 16. Arm 38 extends upwardly from the support bracket 16 functionally. Marking 36 on arm 38 cooperates with markings 39 on the adjoining surface of the second bracket 22 to indicate specifically the relative radial displacement of the second bracket 22 from the zero point, the zero point indicating that the bracket 22 substantially parallel with the longitudinal axis 14 of the base 12.

The first bracket 20 includes a distal mounting surface 40 having a locking mechanism 42 mounted thereon. This locking mechanism 42 is in the form of a lockscrew. Of course, each of the locking mechanisms 26,32,42, can take other forms well known in the art. Each locking mechanism reversibly locks and unlocks the various members associated therewith.

The locking mechanism 42 provides a single point connecting means for connecting a plurality of bone preparing devices, as described below, to the base 12 at a single reference point. The first bracket 20 provides axial adjustment means for axially adjusting the single point connecting means relative to the longitudinal axis 14 of the base 12 and the long axis of the bone upon which the base 12 is mounted. Second bracket 22 provides radial adjustment means for radially adjusting the single point connecting means relative to the base 12 and the distal end of the bone. The markings 30,39 in cooperation with indicating lines 28,36 provide precise quantitative measurement of the axial displacement from the connecting surface or mechanism 42 (and those devices attached thereto) and the zero reference point while indicating reference numerals 39 cooperate with indicating line 36 to quantitatively provide precise radial displacement. As described below in detail, the use of these mechanisms allow for precise alignment of the bone preparing devices attached to the connecting mechanism 42 externally of the bone such that precise alignment preparation of the bone distal end can be made which translates into more accurate placement of the prosthesis device. This further translates into significantly improved function of the implants. The entire base 12 remains noninvasive.

The base 12 includes seating means for seating the base 12 on the bone along the long axis of the bone. The seating means includes two spaced substantially V-shaped surfaces 44 and 46 extending from the bottom surface of the base 12. Of course, the surfaces 44,46 can be made in various shapes to effectively seat the base 12.

More specifically, the L-shaped support member 16 includes a first leg 48 having the support surface 18 thereon defining a top surface of the base 12. The support member further includes a second leg 50 including one of the substantially V-shaped surfaces 44. The base 12 further includes an arm portion 52 extending from the second leg portion 50, the length of the arm portion 52 defining the longitudinal axis 14 of the base 12. The arm portion 52 includes a second one of the substantially U-shaped portions 46 distal from the second leg 16. Of course, the device could include further support surfaces to stabilize the device as needed.

Figure 5:
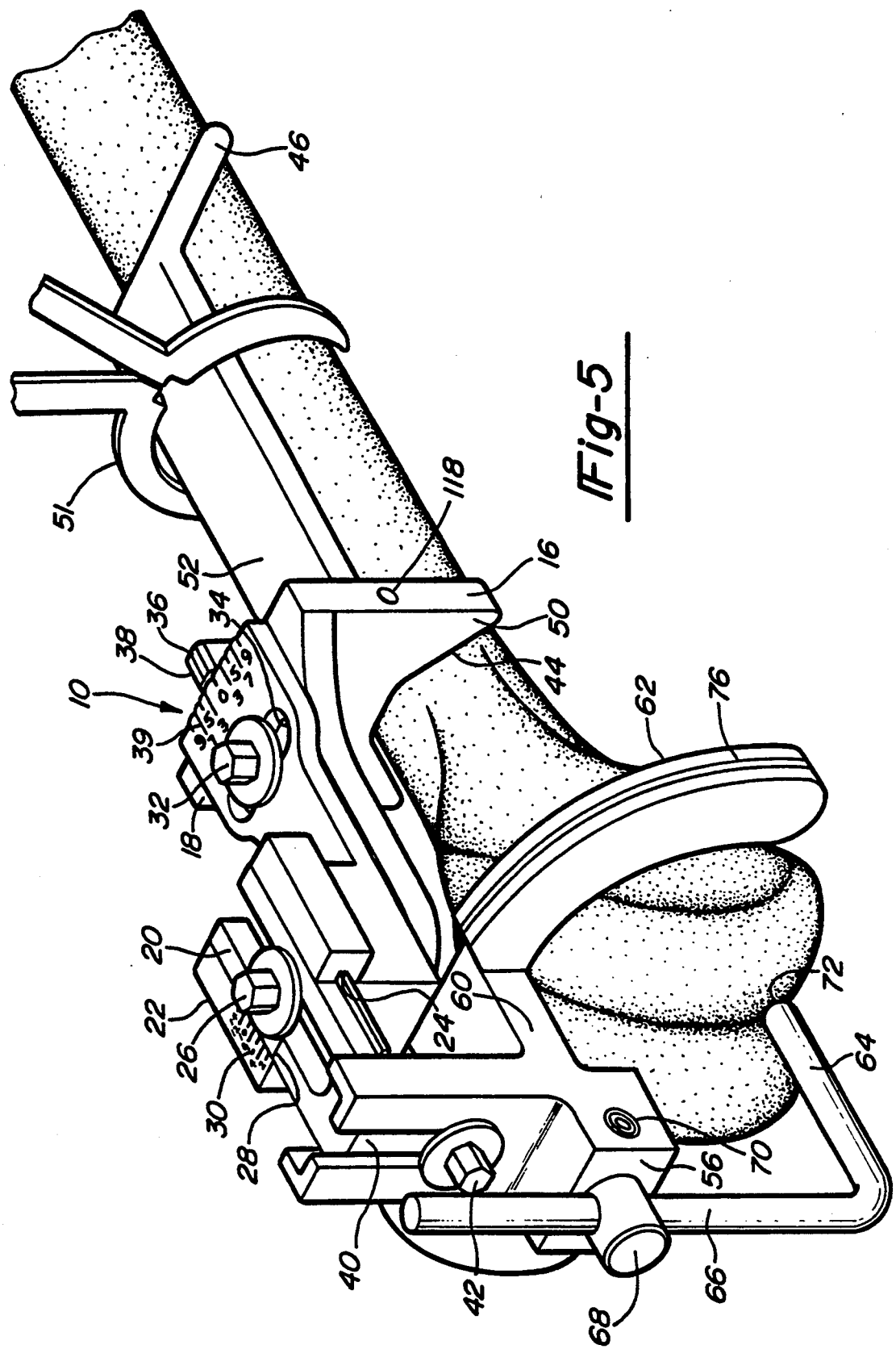
FIG. 5 is a perspective view of the distal cutting component mounted on the base member of the assembly, the assembly being mounted on the distal end of femur.

The article 10 includes mounting means which can be in the form of a state of the art bone clamp 51, as shown in FIGS. 5 through 7 engaging the arm portion 52 for clamping the arm portion 52 about the bone. The bone clamp 51 can take on various forms. However, the mounting function is critical for the function of the device as once the base is appropriately externally mounted (being noninvasive) and the brackets 20,22 are set, the mounting surface 40 becomes a stable landmark for mounting all tool attachments and setting the angle and depth of all cuts made. Accurate cutting of the femur to accept a femoral prosthesis is thereby achieved. The device thereby provides a single point reference device at the locking mechanism 42 which is securely set in place relative to the bone by the mounting means as well as locked axially and radially relative to the distal end of the bone in order to allow for referencing of the external device to accurately place the cuts.

Figure 4:
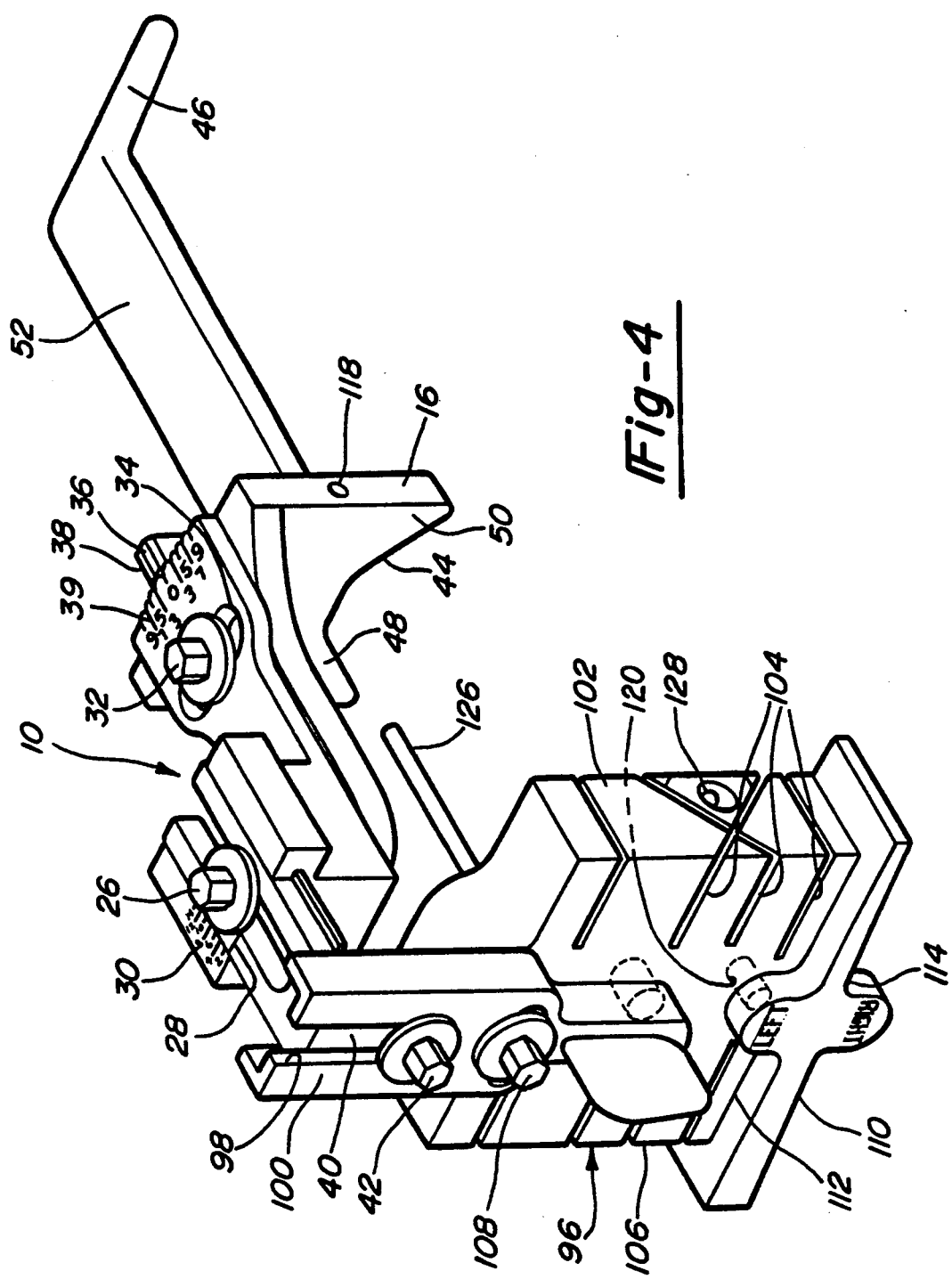
FIG. 4 is a perspective view of the base member having a cutting block component mounted thereon.

Although not at all totally exhaustive of the various types of attachments that can be made to the base 12 for the preparation of a bone to receive a distal implant, the present invention provides three components herein illustrated in FIGS. 1, 3 and 4.

Referring to FIG. 1, a distal cut component is generally shown at 56. The distal cut component 56 includes a mounting slot 58 for engagement by the locking mechanism 42 to connect the distal cut component 56 to the mounting surface 40 of the single point connecting means 42. The distal cut component 56 can be released from the base 16 by loosening of the locking mechanism 42.

The distal cut component 56 includes a body portion 60 and a guide track 62 mounted thereon for guiding a blade of the cutting instrument to make a sagittal cut at the distal end of the bone. Such cutting instruments (osteotomy saws) are well known in the art.

L-shaped rod member 64 provides referencing means for referencing the guide track 62 vis-a-vis the distal end of the bone to set a zero point reference at a most distal end of the bone. More specifically, the L-shaped rod member 64 includes a first arm 66 pivotally connected to the base portion 60 of the distal cut component. The rod member 64 is connected to an axle 68 which can be fixed from rotation by a ball plunger of a set screw 70. The rod member 64 includes a second arm portion 72 having an end portion 74 which is coplanar with the slot 76 in the guide track 62 which receives the saw blade. Accordingly, as more fully described below, alignment of the end portion 74 with the distal most surface of the bone to be resected aligns the guide track 62 with the same distal most surface of the bone defining a zero point reference of the guide track relative to the bone.

The axial adjustment means comprising the first bracket 20 can be adjusted to set an amount of bone cut and the radial adjustment means defined by the bracket 22 is adjusted to set an angle of the cut relative to the long axis of the bone. Thusly, the quantitative mechanisms of the base 12 (the axial and radial adjustments) are normalized by the reference rod 64 to the distal most portion of the bone. After this normalization, the distance indicators 30,39 can provide accurate measurements of the amount of bone being cut and the angle of the cut.

FIG. 3 shows a planing component generally shown at 78. The planing component 78 planes the sagittally cut surface at the distal end of the bone. This is a critical step to achieve close tolerances between the cut bone surface and the base of the implant. When the bone to be cut is the femur, the fit is critical because of the load bearing function of the implant at the distal end of the bone.

Generally, the planing component 78 includes a tool holder 80, a planing tool 82 operatively connected thereto, and a locking mechanism receiving slot 84 for receiving the locking mechanism 42 thereby connecting the tool holder at the single point connecting means. Similar to the precise placement of the distal cutting component 56, once the distal cutting component 56 is removed, it is replaced by the tool holder 80 thereby setting the planing tool 82 at the same angle as the previously made distal cut.

More specifically, the tool holder 80 includes a pocket 86 defining a cylinder channel therethrough. When the indicator line 36 is aligned with the zero point of indicating lines 39, the channel is parallel with the longitudinal axis 14 of the base 12. The planing tool 82 includes a stem having a smaller diameter portion 88 receivable and releasable from the pocket 86 and axially moveable therein and a larger diameter portion 90 retainable within the pocket 86 and axially moveable therein for locking the planing tool 82 in the tool holder 80 at the predetermined radial orientation relative to the base 12. Of course, the radial adjustment mechanism can be reset for further radial orientation of the planing tool 82 to the sagittal bone cut surface if desired.

The planing tool 82 includes a handle portion 92 which can be gripped by the operator. The planing tool 82 also includes a planing surface 94 which planes the previously cut surface. Such a planing tool can take various other forms and be used independent of the distal cutting component previously described.

A cutting block component mounted on the base 12 is generally shown at 96 in FIG. 4. The cutting block component 96 guides a blade of cutting tool to make cuts on anterior, inferior and posterior surfaces of the distal end of the bone prior to the mounting of the trial prosthesis. Similar to the other components, the cutting block component 96 includes a mounting slot 98 for receiving the locking mechanism 42 thereby connecting the cutting block component 96 to the single point connecting means.

Generally, the cutting block component 96 includes a connector member 100 for connection to the locking mechanism 42 and a block member 102 including a plurality of slots 104 extending therethrough for receiving a blade of cutting device. Examples of such cutting devices are well known in the art.

The cutting block 102 includes a top portion 106 pivotally connected to the connector member 100 by locking mechanism 108. The cutting block component 96 further includes a wedge member 110 connected to the bottom portion 112 of the cutting block 102 and having a bottom surface 114 defining a predetermined angle relative to the bottom portion of the block member 102 whereby the angle allows for a predetermined rotation of the cutting block member relative to the connecting member 100 for the purposes described below. The assembly includes various other pins for securing the device which are described in detail below in relation to the preferred surgical protocol.

The present invention provides a method for preparing the distal end of a bone to receive a distal implant. As discussed above, the device shown in the figures is specifically designed for the preparation of femoral implant.

Generally, the method includes the steps of mounting the base member 12 on the bone and clamping the base member 12 along the long axis of the bone. One of a plurality of bone preparing devices, such as those shown in FIGS. 1, 3, and 4, are connected to the base member 12 at a single reference point defined by locking mechanism 42. The single reference point is axially adjusted relative to the base member 12 and the long axis of the bone by adjustment of the first bracket 22 and locking mechanism 26. The single reference point is adjusted radially relative to the base 12 and the distal end of the bone by adjustment of the second bracket 22 and locking mechanism 32. This method normalizes axial and radial orientation of the bone preparing devices relative to the distal end of the bone.

The preferred surgical procedure is as follows and illustrated in FIGS. 5 through 7. The article 10 is placed onto the long axis of the femur as shown in FIG. 5. At the time of placement, the distal cut component 56 is connected .to the base 12. The reference lines 28,36 are zeroed relative to the guide markings 30,39. The second bracket 22 is then set for a valgus angle desired by the practitioner in view of the anatomic femur. This is accomplished by loosening the locking screw mechanism 32 and rotating the bracket 22 into the desired position which is located by the indicator set at 0°, 3°, 5° etc. As shown in FIGS. 1 and 5, the valgus angle can be set for left or right knees as the indicators go to the left and right of the zero point. The member 38 can include a ball plunger (not shown) which can lock into grooves 116 in the end of the bracket 22 corresponding to the degree variations marked by indications 39. Once the correct valgus angle desired is set, the lockscrew 32 is tightened down.

The guide 10 is slid back and forth referencing the high point on the condyle of the distal end of the knee. This can also be located by rotating the rod 64 by loosening of the lockscrew 70. This allows the end portion 74 of the rod 64 to slide and rotate to find the correct location of the high point of the condyle. Reference is then made in relationship to the patellar track and intercondylar notch of the femur. Once this is done, the high point of the condyle is then rechecked and the bracket is locked in place by pins disposed through pin holes 118 and by the clamp 51 around the arm portion 52 about the bone.

Once this is done, the distal cut component has been set for a zero amount of bone at the high point of the condyle. The amount of bone to be taken can be adjusted by loosening the lockscrew 26 and adjusting the reference indicator 28 to correct amount of bone to be removed in 2 millimeter increments as indicated by reference numerals 30. The amount of bone to be taken from the distal surface is set by the thickness of the implant distal surface. The depths are 6 millimeters for a − small, + small, medium and medium +, 7 mm for a − large and + large, and 8 mm for an − extra large femoral component as normally used. Once the distal cut component has been set, the distal cut is then made. The cut matches the thickness replaced by the prosthesis.

After the distal cut has been made, the lockscrew mechanism 42 is loosened and the distal cut component is removed along with the rod 64 attached thereto. If the rod member 64 is determined to be cumbersome or in the way, it can be rotated by loosening of the setscrew 70 or completely removed by removal of the axial 68 the base 60.

The planing component 78 is slid onto the surface 40 by mating of the slot 84 with the locking screw 42 as shown in FIG. 6. The channel 86 of the tool holder 80 is set at a location of about the center of the distal cut of the femur. Once this is done, the planing tool 82 is slipped in from the side and slipped forward to engage the larger diameter portion 90 within the pocket 86. This allows for precision planing of the distal surface of the bone and is still accurate in relationship to the single point reference. Once planing is complete, the planing tool 82 and tool holder 80 are removed from the base 12.

The final procedure is to place the cutting block component 96 onto the locking surface 40 by mating of the slot 98 with the locking screw 42 and tightening the locking screw 42. The connecting member 100 is slid all the way up along the slot 98 relative to the locking screw 42 in order to visualize the posterior condyles of the tibia. The locking screw mechanism 42 is then hand tightened to hold it in place while various checks are made. The wedge member 110 is used to set the external rotation of the cutting block member 102 and is placed in a hole 120 on the top portion 106 of the cutting block member 102. The wedge allows for a setting of 4° of external rotation and is marked left and right such that it can be used for the left or right knee. This 4° rotation normalizes or evens the condyles relative to the cuts that are about to be made and thereby to the prosthesis that will be mounted. This adjustment corrects the cuts to be made and thereby the placement of the femoral prosthesis to allow for improved patella load bearing characteristics. The adjustment allows for setting of the external rotation required to place the implant accurately and reduce patella tendon forces. The instrument actually utilizes the posterior condyle as a line of site reference to correct set the proper external rotation such that this external rotation, in combination with the axial alignment and valgus alignment already provided by the system in total provides reduced tendon forces on the patella.

Specifically, once the wedge 110 is placed on the cutting block 102, the lockscrew 108 is loosened and the block rotated to achieve equal amounts of posterior condyle exposure beneath the bottom surface 114 of the wedge 110. This is achieved by relative movement of the locking screw 108 through slot 124. Once external rotation has been set, the lockscrew is tightened down and the external rotation will remain set in this position.

In order to accurately place the anterior cut on the femur in order to not notch the femur, a pin 126 is placed through the block member 102. The locking mechanism screw 42 is loosened, allowing the entire cutting block component 96 to slide down until the pin rests in the patella track of the femur. This references the deepest point equal to the edge of the long axis of the femur. Once this is in place, the locking screw mechanism 42 is tightened and the cutting block component 96 is now set in the correct position to make the cuts. At this point, locking screw mechanism 26 is loosened and the cutting block component 96 is slid against the distal surface of the bone. The block member 102 is pinned in place by pins disposed through pin holes 128, the mounted pins (not shown) providing for decreased vibration of the cutting block member 102 and secured positioning. The anterior, posterior, and bevel cuts are then made. Once this is complete, the locking screw mechanism 42 is loosened, the pins removed, and the entire cutting block component 96 is removed for proper trialing of the implant before the base 12 is removed.

The maintenance of the base 12 in place is very useful if revision is required. For example, if revision is required, such as the need for posterior stabilization, separate further components can be mounted on the base 12 for the further operations and the cuts can be accurately placed with respect to current cuts.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. An external alignment system for preparing a bone to receive a distal implant, said system comprising:

a base having a longitudinal axis;

mounting means for mounting said base on the external surface of the bone aligning said longitudinal axis of said base parallel with a long axis of the bone;

single point connecting means for connecting a plurality of bone preparing devices to said base at a single point reference;

a cutting guide component for guiding a blade of a cutting tool to make cuts on the distal end of the bone, said cutting guide component including a guide member having a slot for receiving a blade of a cutting tool and including a cutting guide component connecting means for connecting said guide member relative to said single point connecting means and for allowing said guide member to rotate relative to said base about an axis substantially parallel to said longitudinal axis of said base;

axial adjustment means for axially adjusting said single point connecting means relative to said base along said longitudinal axis of said base and the long axis of the bone; and radial adjustment means for radially adjusting said single point connecting means relative to said base and the distal end of the bone.

2. A system as set forth in claim 1 wherein said base includes a support surface and a pair of connected brackets mounted thereon, a first of said brackets being axially adjustable relative to said base along said longitudinal axis of said base and defining said axial adjustment means and a second of said brackets being radially adjustable relative to said base, one of said first and second brackets being operatively connected to said support surface and said single point connecting means being connected to one of said first and second brackets.

3. A system as set forth in claim 2 wherein said base includes a top surface and a bottom surface, said second bracket being operatively connected to said support surface for pivoting movement relative thereto and said base including first locking means for locking said second bracket relative to said support surface, said first bracket being operatively connected to said second bracket for axial movement away from and towards said second bracket, said base including second locking means for locking said first bracket in place relative to said second bracket, said first bracket including a mounting surface distal relative to said second bracket and including a locking mechanism mounted on said mounting surface for locking the plurality of bone preparing devices to said first bracket at said single point reference whereby said single point reference can be adjusted radially and axially relative to said base.

4. A system as set forth in claim 3 wherein said base includes seating means for seating said base on the bone along the long axis of the bone, said seating means including at least two spaced and substantially V-shaped surfaces extending from said bottom surface of said base.

5. A system as set forth in claim 4 wherein said base includes an L-shaped portion including a first leg having said support surface thereon defining said top surface of said base and a second leg including one of said substantially V-shaped surfaces, said base further including an arm portion extending from said second leg defining said longitudinal axis of said base, said arm portion including a second one of said substantially V-shaped portions distal from said second leg.

6. A system as set forth in claim 5 wherein said mounting means includes a bone clamp engaging said arm portion for clamping said arm portion to the bone.

7. A system as set forth in claim 1 including a distal cut component for making a sagittal cut at the distal end of the bone, said distal cut component including a distal cut component connecting means for connecting said distal cut component to said single point connecting means.

8. A system as set forth in claim 7 including a guide track for guiding a blade of a cutting instrument to make the sagittal cut and referencing means for referencing said guide track visa vis the distal end of the bone to set a zero point reference at a most distal end of the bone whereby said axial adjustment means is adjusted to set an amount of bone cut and radial adjustment means to adjust and set an angle of the cut relative to the long axis of the bone.

9. A system as set forth in claim 1 including a planing component for planing a sagittally cut surface at the distal end of the bone, said planing component including a tool holder, a planing tool operatively connected thereto, and connecting means for connecting said tool holder to said single point connecting means and for allowing adjustment of said radial adjustment means to adjust the radial orientation of said planing tool relative to the sagittally cut bone surface.

10. A system as set forth in claim 1 wherein said guide member has a bottom portion and wherein said cutting guide component includes a wedge member connected to said bottom portion of said guide member and having a surface defining a predetermined angle relative to said bottom portion of said guide member whereby said surface provides a line of site reference point to permit a predetermined rotation of said guide component relative to said base.

11. A system for preparing a bone to receive a distal implant, said system comprising:
a base having a longitudinal axis;
mounting means for mounting said base on the bone aligning said longitudinal axis of said base parallel with a long axis of the bone;
single point connecting means for connecting a plurality of bone preparing devices to said base at a single point reference;
axial adjustment means for axially adjusting said single point connecting means relative to said base along said longitudinal axis of said base and the bone;
radial adjustment means for radially adjusting said single point connecting means relative to said base and the distal end of the bone;
a distal cut component for making a sagittal cut at the distal end of the bone, said distal cut component including connecting means for connecting said distal cut component to said single point connecting means;
a guide track for guiding a blade of a cutting, instrument to make the sagittal cut; and
referencing means for referencing said guide track vis a vis the distal end of the bone to set a zero point reference at a most distal end of the bone whereby said axial adjustment means is adjusted to set an amount of bone cut and radial adjustment means to adjust and set an angle of the cut relative to the long axis of the bone; said referencing means including a substantially L-shaped rod member including a first arm portion pivotally connected to said distal cut component and a second arm portion having an end portion co-planar with said guide track whereby alignment of said end portion with the distal most surface of the bone aligns said guide track with the distal most surface of the bone defining the zero point reference.

12. A system for preparing a bone to receive a distal implant, said system comprising:
a base having a longitudinal axis;
mounting means for mounting said base on the bone aligning said longitudinal axis of said base parallel with a long axis of the bone;
single point connecting means for connecting a plurality of bone preparing devices to said base at a single point reference;
axial adjustment means for axially adjusting said single point connecting means relative to said base along said longitudinal axis of said base and the long axis of the bone;
radial adjustment means for radially adjusting said single point connecting means relative to said base and the distal end of the bone; and a planing component for planing a sagittally cut surface at the distal end of the bone, said planing component including a tool holder, a planing tool operatively connected thereto, and connecting means for connecting said tool holder to said single point connecting means; said tool holder including a pocket defining a channel, said planing tool including a stem having a smaller diameter portion receivable and releasable from said pocket and axially movable therein and a larger diameter portion retainable within said pocket and axially movable therein for locking said planing tool in said tool holder at a predetermined radial orientation relative to said base, said radial adjustment means adjusting the radial orientation of said planing tool relative to the sagittally cut bone surface.

13. A method for preparing a distal end of a bone to receive a distal implant, said method including the steps of:

mounting a base member on and external to the bone and clamping the base member along the long axis of the bone;

connecting a distal cut component to the base member at a single reference point, the distal cut component including a guide track for guiding a blade of a cutting tool and a reference rod having an end portion co-planar with the guide track;

axially adjusting the single reference point relative to the base and the long axis of the bone;

radially adjusting the single reference point relative to the base and distal end of the bone thereby normalizing the axial and radial orientation of the distal cut component relative to the distal end of the bone;

axially and radially adjusting the end portion of the reference rod to a most distal surface of the bone to set a zero point and radial angular reference of the guide track and axially adjusting the single point reference a known amount to set a known amount of bone cut;

removing the distal cut component from the base and connecting a planing component to the base at the previously adjusted single point reference and planing the previously cut surface flat at the previously set radial angle; and removing the planing component from the base and connecting a cutting block component having a bottom surface to the base at the axially and radially set single reference point, and externally pivoting the cutting block component relative to the base to achieve equal amounts of bone exposure beneath the bottom surface of the cutting block component.

14. A system for preparing a bone to receive an implant, said system comprising:

a base having a longitudinal axis;

mounting means for mounting said base on the bone aligning said longitudinal axis of said base parallel with a long axis of the bone;

single point connecting means for connecting a plurality of bone preparing devices to said base at a single point reference;

axial adjustment means for axially adjusting said single point connecting means relative to said base along said longitudinal axis of said base and the long axis of the bone;

radial adjustment means for radially adjusting said single point connecting means relative to said base and the bone;

a cut component for making a cut in the bone, said cut component including a cut component connecting means for connecting said cut component to said single point connecting means;

a guide track for guiding a blade of a cutting instrument to make the cut; and referencing means for referencing said guide track visa vis the bone to set a zero point reference at a reference point of the bone whereby said axial adjustment means is adjusted to set an amount of bone cut and radial adjustment means to adjust and set an angle of the cut relative to the long axis of the bone; said referencing means including a first portion pivotally connected to said cut component and a second portion having an end portion co-planar with said guide track whereby alignment of said end portion with the reference point of the bone aligns said guide track with the reference point of the bone defining the zero point reference.

15. A system for preparing a bone to receive an implant, said system comprising:

a base having a longitudinal axis;

mounting means for mounting said base on the bone aligning said longitudinal axis of said base parallel with a long axis of the bone;

single point connecting means for connecting a plurality of bone preparing devices to said base at a single point reference;

axial adjustment means for axially adjusting said single point connecting means relative to said base along said longitudinal axis of said base and the long axis of the bone;

radial adjustment means for radially adjusting said single point connecting means relative to said base and the bone; and a planing component for planing a cut surface in the bone, said planing component including a tool holder, a planing tool operatively connected thereto, and connecting means for connecting said tool holder to said single point connecting means; said tool holder having a channel, said planing tool including a stem having a first portion receivable and releasable from said channel and axially movable therein and a second portion retainable within said channel and axially movable therein for locking said planing tool in said tool holder at a predetermined radial orientation relative to said base, said radial adjustment means adjusting the radial orientation of said planing tool relative to the cut surface in the bone.

* * * * *